United States Patent
Aysta et al.

(10) Patent No.: US 8,080,409 B2
(45) Date of Patent: *Dec. 20, 2011

(54) SAMPLE PROCESSING DEVICE COMPRESSION SYSTEMS AND METHODS

(75) Inventors: James E. Aysta, Stillwater, MN (US); William Bedingham, Woodbury, MN (US); Barry W. Robole, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/793,714

(22) Filed: Jun. 4, 2010

(65) Prior Publication Data

US 2010/0240124 A1 Sep. 23, 2010

Related U.S. Application Data

(63) Continuation of application No. 11/174,757, filed on Jul. 5, 2005, now Pat. No. 7,754,474.

(51) Int. Cl.
*C12M 3/00* (2006.01)

(52) U.S. Cl. .................. 435/287.2; 435/287.3; 435/809; 374/24; 374/51

(58) Field of Classification Search ............... 435/287.2, 435/287.3, 809; 374/24, 51
See application file for complete search history.

(56) References Cited

U.S. PATENT DOCUMENTS

| | | | |
|---|---|---|---|
| 3,555,284 A | 1/1971 | Anderson | |
| 3,713,124 A | 1/1973 | Durland et al. | |
| 3,795,451 A | 3/1974 | Mailen | |
| 3,798,459 A | 3/1974 | Anderson et al. | |
| 3,856,470 A | 12/1974 | Cullis et al. | |
| 3,873,217 A | 3/1975 | Anderson et al. | |
| 3,912,799 A | 10/1975 | Chisholm | |
| 3,964,867 A | 6/1976 | Berry | |
| 4,030,834 A | 6/1977 | Bauer et al. | |
| 4,046,511 A | 9/1977 | Stabile | |
| 4,111,304 A | 9/1978 | Lucas | |
| 4,123,173 A | 10/1978 | Bullock et al. | |
| 4,244,916 A | 1/1981 | Guigan | |

(Continued)

FOREIGN PATENT DOCUMENTS

CA 2130013 3/1999

(Continued)

OTHER PUBLICATIONS

U.S. Appl. No. 60/237,151, filed Oct. 2, 2000.

(Continued)

*Primary Examiner* — William H Beisner
*Assistant Examiner* — Michael Hobbs
(74) *Attorney, Agent, or Firm* — Nicole J. Einerson (57) ABSTRACT

Sample processing systems and methods of using those systems for processing sample materials located in sample processing devices are disclosed. The sample processing systems include a rotating base plate on which the sample processing devices are located during operation of the systems. The systems also include a cover and compression structure designed to force a sample processing device towards the base plate. The preferred result is that the sample processing device is forced into contact with a thermal structure on the base plate. The systems and methods of the present invention may include one or more of the following features to enhance thermal coupling between the thermal structure and the sample processing device: a shaped transfer surface, magnetic compression structure, and floating or resiliently mounted thermal structure. The methods may preferably involve deformation of a portion of a sample processing device to conform to a shaped transfer surface.

24 Claims, 4 Drawing Sheets

U.S. PATENT DOCUMENTS

| | | |
|---|---|---|
| 4,252,538 A | 2/1981 | Barr |
| 4,256,696 A | 3/1981 | Soodak |
| 4,298,570 A | 11/1981 | Lillig et al. |
| 4,384,193 A | 5/1983 | Kledzik et al. |
| 4,390,499 A | 6/1983 | Curtis et al. |
| 4,396,579 A | 8/1983 | Schroeder et al. |
| D271,993 S | 12/1983 | Swartz |
| 4,456,581 A | 6/1984 | Edelmann et al. |
| D274,553 S | 7/1984 | Perry |
| 4,476,733 A | 10/1984 | Chlosta et al. |
| 4,488,810 A | 12/1984 | Hatanaka et al. |
| 4,498,896 A | 2/1985 | Leis |
| D277,891 S | 3/1985 | Uffenheimer et al. |
| 4,554,436 A | 11/1985 | Chlosta et al. |
| 4,580,896 A | 4/1986 | Brickus et al. |
| 4,632,908 A | 12/1986 | Schultz |
| D288,124 S | 2/1987 | Brickus et al. |
| 4,673,657 A | 6/1987 | Christian |
| 4,695,430 A | 9/1987 | Coville et al. |
| 4,814,279 A | 3/1989 | Sugaya |
| 4,839,296 A | 6/1989 | Kennedy et al. |
| 4,906,432 A | 3/1990 | Geiselman |
| 4,933,146 A | 6/1990 | Meyer et al. |
| 4,981,801 A | 1/1991 | Suzuki et al. |
| 4,990,075 A | 2/1991 | Wogoman |
| 5,049,591 A | 9/1991 | Hayashi et al. |
| 5,079,155 A | 1/1992 | Cox et al. |
| 5,086,337 A | 2/1992 | Noro et al. |
| 5,128,197 A | 7/1992 | Kobayashi et al. |
| 5,135,786 A | 8/1992 | Hayashi et al. |
| 5,139,832 A | 8/1992 | Hayashi et al. |
| D329,024 S | 9/1992 | Marks |
| 5,145,935 A | 9/1992 | Hayashi |
| 5,149,505 A | 9/1992 | English et al. |
| 5,154,888 A | 10/1992 | Zander et al. |
| 5,182,083 A | 1/1993 | Barker et al. |
| 5,207,987 A | 5/1993 | Kureshy et al. |
| 5,219,526 A | 6/1993 | Long |
| 5,229,297 A | 7/1993 | Schnipelsky et al. |
| 5,254,479 A | 10/1993 | Chemelli |
| 5,258,163 A | 11/1993 | Krause et al. |
| 5,264,184 A | 11/1993 | Aysta et al. |
| 5,278,377 A | 1/1994 | Tsai |
| 5,281,516 A | 1/1994 | Stapleton et al. |
| 5,288,463 A | 2/1994 | Chemelli |
| 5,310,523 A | 5/1994 | Smethers et al. |
| 5,336,467 A | 8/1994 | Heidt et al. |
| 5,411,065 A | 5/1995 | Meador et al. |
| 5,415,839 A | 5/1995 | Zaun et al. |
| 5,422,271 A | 6/1995 | Chen et al. |
| 5,429,810 A | 7/1995 | Knaepler et al. |
| 5,438,128 A | 8/1995 | Nieuwkerk et al. |
| 5,439,649 A | 8/1995 | Tseung et al. |
| 5,446,270 A | 8/1995 | Chamberlain et al. |
| 5,460,780 A | 10/1995 | Devaney, Jr. et al. |
| 5,461,134 A | 10/1995 | Leir et al. |
| 5,464,541 A | 11/1995 | Aysta et al. |
| 5,496,518 A | 3/1996 | Arai et al. |
| 5,496,520 A | 3/1996 | Kelton et al. |
| 5,527,931 A | 6/1996 | Rich et al. |
| 5,529,708 A | 6/1996 | Palmgren et al. |
| 5,571,410 A | 11/1996 | Swedberg et al. |
| 5,578,270 A | 11/1996 | Reichler et al. |
| 5,587,128 A | 12/1996 | Wilding et al. |
| 5,593,838 A | 1/1997 | Zanzucchi et al. |
| 5,599,501 A | 2/1997 | Carey et al. |
| 5,601,141 A | 2/1997 | Gordon et al. |
| 5,604,130 A | 2/1997 | Warner et al. |
| 5,616,301 A | 4/1997 | Moser et al. |
| 5,637,469 A | 6/1997 | Wilding et al. |
| 5,639,428 A | 6/1997 | Cottingham |
| 5,639,810 A | 6/1997 | Smith, III et al. |
| 5,691,208 A | 11/1997 | Miltenyi et al. |
| RE35,716 E | 1/1998 | Stapleton et al. |
| 5,720,923 A | 2/1998 | Haff et al. |
| 5,721,123 A | 2/1998 | Hayes et al. |
| 5,726,026 A | 3/1998 | Wilding et al. |
| 5,792,372 A | 8/1998 | Brown et al. |
| 5,795,547 A | 8/1998 | Moser et al. |
| 5,800,785 A | 9/1998 | Bochner |
| 5,804,141 A | 9/1998 | Chianese |
| 5,811,296 A | 9/1998 | Chemelli et al. |
| 5,819,842 A | 10/1998 | Potter et al. |
| 5,822,903 A | 10/1998 | Davis, Sr. |
| 5,833,923 A | 11/1998 | McClintock et al. |
| 5,856,194 A | 1/1999 | Arnquist et al. |
| 5,863,502 A | 1/1999 | Southgate et al. |
| 5,863,801 A | 1/1999 | Southgate et al. |
| 5,869,002 A | 2/1999 | Limon et al. |
| 5,876,675 A | 3/1999 | Kennedy |
| 5,886,863 A | 3/1999 | Nagasaki et al. |
| 5,922,617 A | 7/1999 | Wang et al. |
| 5,925,455 A | 7/1999 | Bruzzone et al. |
| 5,948,227 A | 9/1999 | Dubrow |
| 5,976,468 A | 11/1999 | Godec et al. |
| 5,997,818 A | 12/1999 | Hacker et al. |
| 6,001,643 A | 12/1999 | Spaulding |
| 6,007,690 A | 12/1999 | Nelson et al. |
| 6,007,914 A | 12/1999 | Joseph et al. |
| 6,013,513 A | 1/2000 | Reber et al. |
| 6,030,581 A | 2/2000 | Virtanen |
| 6,048,457 A | 4/2000 | Kopaciewicz et al. |
| 6,063,589 A | 5/2000 | Kellogg et al. |
| 6,068,751 A | 5/2000 | Neukermans |
| 6,074,827 A | 6/2000 | Nelson et al. |
| 6,093,370 A | 7/2000 | Yasuda et al. |
| 6,103,199 A | 8/2000 | Bjornson et al. |
| 6,143,247 A | 11/2000 | Sheppard, Jr. et al. |
| 6,143,248 A | 11/2000 | Kellogg et al. |
| 6,153,012 A | 11/2000 | Rupp et al. |
| 6,168,759 B1 | 1/2001 | Green et al. |
| 6,168,948 B1 | 1/2001 | Anderson et al. |
| 6,183,693 B1 | 2/2001 | Bogen et al. |
| 6,184,029 B1 | 2/2001 | Wilding et al. |
| 6,190,617 B1 | 2/2001 | Clark et al. |
| 6,197,595 B1 | 3/2001 | Anderson et al. |
| 6,200,474 B1 | 3/2001 | Kopaciewicz et al. |
| D441,873 S | 5/2001 | Köhler |
| 6,265,168 B1 | 7/2001 | Gjerde et al. |
| 6,284,113 B1 | 9/2001 | Bjornson et al. |
| 6,296,809 B1 | 10/2001 | Richards et al. |
| 6,302,134 B1 | 10/2001 | Kellogg et al. |
| 6,306,273 B1 | 10/2001 | Wainright et al. |
| 6,319,469 B1 | 11/2001 | Mian et al. |
| 6,344,326 B1 | 2/2002 | Nelson et al. |
| 6,375,898 B1 | 4/2002 | Ulrich et al. |
| 6,391,264 B2 | 5/2002 | Hammer et al. |
| 6,399,025 B1 | 6/2002 | Chow |
| 6,413,782 B1 | 7/2002 | Parce et al. |
| 6,432,365 B1 | 8/2002 | Levin et al. |
| 6,440,725 B1 | 8/2002 | Pourahmadi et al. |
| 6,450,047 B2 | 9/2002 | Swedberg et al. |
| 6,451,260 B1 | 9/2002 | Düsterhöft et al. |
| 6,461,287 B1 | 10/2002 | Glater |
| 6,465,225 B1 | 10/2002 | Fuhr et al. |
| 6,467,275 B1 | 10/2002 | Ghoshal |
| 6,479,300 B1 | 11/2002 | Jiang et al. |
| 6,527,432 B2 | 3/2003 | Kellogg et al. |
| 6,532,997 B1 | 3/2003 | Bedingham et al. |
| 6,548,788 B2 | 4/2003 | Kellogg et al. |
| 6,558,947 B1 | 5/2003 | Lund et al. |
| 6,565,808 B2 | 5/2003 | Hudak et al. |
| 6,566,637 B1 | 5/2003 | Revesz et al. |
| 6,572,830 B1 | 6/2003 | Burdon et al. |
| 6,582,662 B1 | 6/2003 | Kellogg et al. |
| 6,593,143 B1 | 7/2003 | Gordon |
| 6,617,136 B2 | 9/2003 | Parthasarathy et al. |
| 6,627,159 B1 | 9/2003 | Bedingham et al. |
| 6,632,399 B1 | 10/2003 | Kellogg et al. |
| 6,645,758 B1 | 11/2003 | Schnipelsky et al. |
| 6,648,853 B1 | 11/2003 | McEntee |
| 6,660,147 B1 | 12/2003 | Woudenberg et al. |
| 6,664,104 B2 | 12/2003 | Pourahmadi et al. |
| 6,692,596 B2 | 2/2004 | Moll et al. |
| 6,706,519 B1 | 3/2004 | Kellogg et al. |
| 6,720,187 B2 | 4/2004 | Bedingham et al. |
| 6,723,236 B2 | 4/2004 | Fisk et al. |

| | | | | | | |
|---|---|---|---|---|---|---|
| 6,730,516 | B2 | 5/2004 | Jedrzejewski et al. | EP | 0693560 | 1/1996 |
| 6,734,401 | B2 | 5/2004 | Bedingham et al. | EP | 0 807 468 A2 | 11/1997 |
| 6,780,818 | B2 | 8/2004 | Gundel et al. | EP | 0807486 | 11/1997 |
| 6,814,935 | B2 | 11/2004 | Harms et al. | EP | 0 810 030 A1 | 12/1997 |
| 6,824,738 | B1 | 11/2004 | Neeper et al. | EP | 0 965 388 | 12/1999 |
| 6,889,468 | B2 | 5/2005 | Bedingham et al. | EP | 1 010 979 A1 | 6/2000 |
| 6,987,253 | B2 | 1/2006 | Bedingham et al. | EP | 0 807 486 B1 | 12/2001 |
| 7,026,168 | B2 | 4/2006 | Bedingham et al. | EP | 0 810 030 B1 | 3/2003 |
| 7,164,107 | B2 | 1/2007 | Bedingham et al. | EP | 1 010 979 B1 | 10/2003 |
| 7,192,560 | B2 | 3/2007 | Parthasarathy et al. | JP | 6-057259 | 4/1985 |
| 7,273,591 | B2 | 9/2007 | Sellers et al. | JP | 9-72912 | 3/1997 |
| D557,425 | S | 12/2007 | Nakamura et al. | JP | 11124419 | 5/1999 |
| D559,993 | S | 1/2008 | Nagakubo et al. | JP | 2003-504637 | 2/2003 |
| D559,994 | S | 1/2008 | Nagakubo et al. | JP | 2004-525339 | 8/2004 |
| D560,284 | S | 1/2008 | Nagakubo et al. | JP | 2005-514014 | 5/2005 |
| 7,322,254 | B2 | 1/2008 | Bedingham et al. | JP | 2005-274241 | 10/2005 |
| 7,323,660 | B2 | 1/2008 | Bedingham et al. | JP | 2009-216395 | 9/2009 |
| 7,332,326 | B1 | 2/2008 | Kellogg et al. | WO | WO 91/19567 A1 | 12/1991 |
| D564,667 | S | 3/2008 | Bedingham et al. | WO | WO 94/26414 A1 | 11/1994 |
| 7,396,508 | B1 | 7/2008 | Richards et al. | WO | WO 94/29400 A1 | 12/1994 |
| 7,435,933 | B2 | 10/2008 | Bedingham et al. | WO | WO 95/18676 A1 | 7/1995 |
| 7,569,186 | B2 | 8/2009 | Bedingham et al. | WO | WO 95/19781 | 7/1995 |
| D600,722 | S | 9/2009 | Yabe et al. | WO | WO 96/15576 A1 | 5/1996 |
| D605,206 | S | 12/2009 | Yabe et al. | WO | WO 96/34028 A1 | 10/1996 |
| 7,628,954 | B2 | 12/2009 | Gomm et al. | WO | WO 96/34029 A1 | 10/1996 |
| 7,763,210 | B2 | 7/2010 | Bedingham et al. | WO | WO 96/35458 A2 | 11/1996 |
| 7,767,937 | B2 | 8/2010 | Bedingham et al. | WO | WO 96/41864 A1 | 12/1996 |
| 2001/0045000 | A1 | 11/2001 | Gundel et al. | WO | WO 97/00230 | 1/1997 |
| 2002/0047003 | A1 | 4/2002 | Bedingham et al. | WO | WO 97/21090 A1 | 6/1997 |
| 2002/0048533 | A1 | 4/2002 | Harms et al. | WO | WO 97/46707 A2 | 12/1997 |
| 2002/0064885 | A1 | 5/2002 | Bedingham et al. | WO | WO 97/46707 A3 | 12/1997 |
| 2002/0097632 | A1 | 7/2002 | Kellogg | WO | WO 98/04909 | 2/1998 |
| 2003/0013203 | A1 | 1/2003 | Jedrzejewski et al. | WO | WO 98/07019 A1 | 2/1998 |
| 2003/0017567 | A1 | 1/2003 | Parthasarathy et al. | WO | WO 98/49340 A1 | 11/1998 |
| 2003/0044322 | A1 | 3/2003 | Andersson et al. | WO | WO 98/50147 A1 | 11/1998 |
| 2003/0053934 | A1 | 3/2003 | Andersson et al. | WO | WO 98/53311 A2 | 11/1998 |
| 2003/0118804 | A1 | 6/2003 | Bedingham et al. | WO | WO 99/09394 A1 | 2/1999 |
| 2003/0120062 | A1 | 6/2003 | Parthasarathy et al. | WO | WO 99/15876 | 4/1999 |
| 2003/0124506 | A1 | 7/2003 | Bedingham et al. | WO | WO 99/15888 | 4/1999 |
| 2003/0138779 | A1 | 7/2003 | Parthasarathy et al. | WO | WO 99/40174 | 8/1999 |
| 2003/0139550 | A1 | 7/2003 | Savu et al. | WO | WO 99/44740 A1 | 9/1999 |
| 2003/0152491 | A1 | 8/2003 | Kellogg et al. | WO | WO 99/46591 | 9/1999 |
| 2003/0152994 | A1 | 8/2003 | Woudenberg et al. | WO | WO 99/55827 A1 | 11/1999 |
| 2003/0155034 | A1 | 8/2003 | De Beukeleer et al. | WO | WO 99/58245 A1 | 11/1999 |
| 2003/0228706 | A1 | 12/2003 | Ramstad et al. | WO | WO 99/67639 A1 | 12/1999 |
| 2003/0231878 | A1 | 12/2003 | Shigeura | WO | WO 00/05582 A2 | 2/2000 |
| 2004/0016702 | A1 | 1/2004 | Hennessy et al. | WO | WO 00/40750 A1 | 7/2000 |
| 2004/0016898 | A1 | 1/2004 | Cox et al. | WO | WO 00/45180 | 8/2000 |
| 2004/0018116 | A1 | 1/2004 | Desmond et al. | WO | WO 00/50172 A1 | 8/2000 |
| 2004/0018117 | A1 | 1/2004 | Desmond et al. | WO | WO 00/50642 A1 | 8/2000 |
| 2004/0023371 | A1 | 2/2004 | Fawcett | WO | WO 00/62051 | 10/2000 |
| 2004/0121471 | A1 | 6/2004 | Dufresne et al. | WO | WO 00/68336 A1 | 11/2000 |
| 2004/0179974 | A1 | 9/2004 | Bedingham et al. | WO | WO 00/69560 A1 | 11/2000 |
| 2004/0209258 | A1 | 10/2004 | Parthasarathy et al. | WO | WO 00/78455 A1 | 12/2000 |
| 2005/0028587 | A1 | 2/2005 | Baer | WO | WO 00/79285 A2 | 12/2000 |
| 2005/0036911 | A1 | 2/2005 | Sellers et al. | WO | WO 01/06228 | 1/2001 |
| 2005/0130177 | A1 | 6/2005 | Bedingham et al. | WO | WO 01/07892 A1 | 2/2001 |
| 2005/0142563 | A1 | 6/2005 | Haddad et al. | WO | WO 01/12327 | 2/2001 |
| 2005/0142570 | A1 | 6/2005 | Parthasarathy et al. | WO | WO 01/30995 | 5/2001 |
| 2005/0142571 | A1 | 6/2005 | Parthasarathy et al. | WO | WO 01/38865 | 5/2001 |
| 2005/0142663 | A1 | 6/2005 | Parthasarathy et al. | WO | WO 02/00347 | 1/2002 |
| 2005/0180890 | A1 | 8/2005 | Bedingham et al. | WO | WO 03/054509 | 7/2003 |
| 2005/0282290 | A1 | 12/2005 | Fujimoto | WO | WO 03/054510 | 7/2003 |
| 2006/0013732 | A1 | 1/2006 | Parthasarathy et al. | WO | WO 03/058224 | 7/2003 |
| 2007/0007270 | A1 | 1/2007 | Bedingham et al. | WO | WO 03/058253 A1 | 7/2003 |
| 2007/0009391 | A1 | 1/2007 | Bedingham et al. | WO | WO 03/093836 | 11/2003 |
| 2007/0010007 | A1 | 1/2007 | Aysta et al. | WO | WO 03/104783 A1 | 12/2003 |
| 2007/0132723 | A1 | 6/2007 | Lurz et al. | WO | WO 2004/010760 | 2/2004 |
| 2007/0142780 | A1 | 6/2007 | Van Lue | WO | WO 2004/011142 | 2/2004 |
| 2008/0050276 | A1 | 2/2008 | Bedingham et al. | WO | WO 2004/011143 A2 | 2/2004 |
| 2008/0152546 | A1 | 6/2008 | Bedingham et al. | WO | WO 2004/011147 A1 | 2/2004 |
| 2009/0068062 | A1 | 3/2009 | Jafari et al. | WO | WO 2004/011148 A2 | 2/2004 |
| 2009/0263280 | A1 | 10/2009 | Bedingham et al. | WO | WO 2004/011149 A1 | 2/2004 |
| | | | | WO | WO 2004/011365 A2 | 2/2004 |
| | | FOREIGN PATENT DOCUMENTS | | WO | WO 2004/011592 A2 | 2/2004 |
| DE | | 3712624 | 11/1988 | WO | WO 2004/011681 A1 | 2/2004 |
| EP | | 0 281 368 | 9/1988 | WO | WO 2004/094672 | 11/2004 |
| EP | | 0169306 | 5/1990 | WO | WO 2005/005045 A1 | 1/2005 |
| EP | | 0402994 | 11/1994 | WO | WO 2005/016532 A2 | 2/2005 |

| WO | WO 2005/016532 A3 | 2/2005 |
| WO | WO 2007/005810 | 1/2007 |
| WO | WO 2007/005853 | 1/2007 |
| WO | WO 2008/134470 | 11/2008 |

OTHER PUBLICATIONS

Chiou et al., "A Closed-Cycle Capillary Polymerase Chain Reaction Machine", Analytical Chemistry, vol. 73, No. 9, May 1, 2001, 2018-2021.

*Handbook of Pressure Sensitive Adhesive Technology,* Donatas Satas (Ed.) $2^{nd}$ Edition, Title page, Publication page, Table of Contents, and p. 172, and Fig. 8-16 on p. 173, Van Nostrand Reinhold, New York, NY 1989.

*Handbook of Pressure Sensitive Adhesive Technology,* $3^{rd}$ Edition, Title page, Publication page, Table of Contents, and pp. 508-517.

Litton Product Brochure; Poly Scientific EC3848 High Speed Slip Ring Capsule; Blacksburg, VA; 2 pgs (Oct. 1999).

Meridian Laboratory Datasheet [online]; Rotocon high performance rotary electrical contacts; 5 pgs [retrieved on Jun. 18, 2002]. Retrieved from the Internet: <http://www.meridianlab.com/>.

Meridian Laboratory Datasheet [online]: Model MM Micro-Minature; 5 pgs. [retrieved on Jul. 19, 2001]. Retrieved from the Internet: <http://www.meridianlab.com/mm.htm>.

Motion Technology Product Guide; Commercial and Military/Aerospace Applications; Blacksburg, VA; 8 pgs. (Jul. 1999).

NIST Grant, Project Brief [online]; A Tools for DNA Diagnostics (Oct. 1998) Integrated, Micro-Sample Preparation System for Genetic Analysis,@ [retrieved on Aug. 5, 2002] 2 pgs. Retrieved form the internet at <http://jazz.nist.gov/atpcf/prjbriefs/prjbrief.cfm?ProjectNumber=98-08-0031>.

*Test Methods for Pressure Sensitive Adhesive Tapes,* Pressure Sensitive Tape Council, (1996) (4 pgs).

Sambrook et al., Molecular Cloning, A laboratory Manual, 2nd Edition, Cold Spring Harbor Laboratory, 1989 (30 pgs) includes Title and copyright pages and Table to Contents.

Emmer, A. et al.; "Wall deactivation with fluorosurfactants for capillary electrophoretic analysis of biomolecules"; Electrophoresis 2001, 22; pp. 660-665.

Garcia, A. et al.; "Comparison of Two Leukocyte Extraction Methods for Cytomegalovirus Antigenemia Assay"; Journal of Clinical Microbiology, Jan. 1996; vol. 34, No. 1; pp. 182-184.

SAMPLE PROCESSING DEVICE COMPRESSION SYSTEMS AND METHODS

CROSS-REFERENCE TO RELATED APPLICATIONS

This is a continuation of U.S. patent application Ser. No. 11/174,757, filed Jul. 5, 2005, issued as U.S. Pat. No. 7,754,474.

FIELD

The present invention relates to systems and methods for using rotating sample processing devices to, e.g., amplify genetic materials, etc.

BACKGROUND

Many different chemical, biochemical, and other reactions are sensitive to temperature variations. Examples of thermal processes in the area of genetic amplification include, but are not limited to, Polymerase Chain Reaction (PCR), Sanger sequencing, etc. One approach to reducing the time and cost of thermally processing multiple samples is to use a device including multiple chambers in which different portions of one sample or different samples can be processed simultaneously. Examples of some reactions that may require accurate chamber-to-chamber temperature control, comparable temperature transition rates, and/or rapid transitions between temperatures include, e.g., the manipulation of nucleic acid samples to assist in the deciphering of the genetic code. Nucleic acid manipulation techniques include amplification methods such as polymerase chain reaction (PCR); target polynucleotide amplification methods such as self-sustained sequence replication (3SR) and strand-displacement amplification (SDA); methods based on amplification of a signal attached to the target polynucleotide, such as "branched chain" DNA amplification; methods based on amplification of probe DNA, such as ligase chain reaction (LCR) and QB replicase amplification (QBR); transcription-based methods, such as ligation activated transcription (LAT) and nucleic acid sequence-based amplification (NASBA); and various other amplification methods, such as repair chain reaction (RCR) and cycling probe reaction (CPR). Other examples of nucleic acid manipulation techniques include, e.g., Sanger sequencing, ligand-binding assays, etc.

Some systems used to process rotating sample processing devices may be described in U.S. Pat. No. 6,889,468 titled MODULAR SYSTEMS AND METHODS FOR USING SAMPLE PROCESSING DEVICES and U.S. Pat. No. 6,734,401 titled ENHANCED SAMPLE PROCESSING DEVICES SYSTEMS AND METHODS (Bedingham et al.)

SUMMARY OF THE INVENTION

The present invention provides sample processing systems and methods of using those systems for processing sample materials located in sample processing devices that are separate from the system. The sample processing systems include a rotating base plate on which the sample processing devices are located during operation of the systems. The systems also include a cover and compression structure designed to force a sample processing device towards the base plate. The preferred result is that the sample processing device is forced into contact with a thermal structure on the base plate.

The systems and methods of the present invention may include one or more of the following features to enhance thermal coupling between the thermal structure and the sample processing device: a shaped transfer surface, magnetic compression structure, and floating or resiliently mounted thermal structure.

In embodiments that include a shaped thermal structure, the thermal structure may preferably be provided with a transfer surface in the form of an annular ring. It may be preferred that the transfer surface have a convex curvature, e.g., similar to the top section of a toroidal body. By providing a shaped transfer surface in connection with a cover and compression structure, thermal coupling efficiency between the thermal structure and the sample processing device may be improved. It may be preferred that the cover include compression rings that force the sample processing device to conform to the shaped transfer surface of the thermal structure.

In embodiments that include magnetic compression structure, the cover and base plate may preferably include magnetic elements that, through magnetic attraction, draw the cover towards the base plate. When a sample processing device is located between the cover and the base plate, the compression may improve thermal coupling between the sample processing device and the thermal structure. The magnets may preferably be permanent magnets. One potential advantage of a magnetic compression system is that the compressive forces may be obtained in an apparatus with relatively low mass—which may be useful in rotating systems.

In embodiments that include a floating or biased thermal structure, the thermal structure may preferably be resiliently biased towards the cover such that force directed downward on the thermal structure (from, e.g., the cover) may move the thermal structure relative to the remainder of the base plate (which may preferably remain stationary). It may be preferred that the thermal structure be attached to the base plate using, e.g., one or more springs to provide the resilient bias and structurally couple the thermal structure to the base plate.

In one aspect, the present invention provides a system for processing sample processing devices, the system including a base plate operatively coupled to a drive system, wherein the drive system rotates the base plate about a rotation axis, wherein the rotation axis defines a z-axis; thermal structure operatively attached to the base plate, wherein the thermal structure includes a transfer surface exposed proximate a first surface of the base plate; a cover facing the transfer surface, wherein the cover includes an inner compression ring and an outer compression ring; compression structure operatively attached to the cover to force the cover in a first direction along the z-axis towards the transfer surface, wherein the inner and outer compression rings contact and urge a sample processing device located between the cover and the transfer surface into contact with transfer surface; and an energy source adapted to deliver thermal energy to the thermal structure while the base plate is rotating about the rotation axis.

In another aspect, the present invention provides a system for processing sample processing devices, the system including a base plate operatively coupled to a drive system, wherein the drive system rotates the base plate about a rotation axis, wherein the rotation axis defines a z-axis; thermal structure operatively attached to the base plate, wherein the thermal structure includes a transfer surface exposed proximate a first surface of the base plate; a cover facing the transfer surface; one or more magnetic elements operatively attached to the cover and base plate, wherein magnetic attraction between the one or more magnetic elements attached to the cover and the base plate draw the cover in a first direction along the z-axis towards the first surface of the base plate such that a sample processing device located between the cover and the base plate is urged into contact with the thermal structure of the base plate; and an energy source adapted to deliver thermal energy to the thermal structure while the base plate is rotating about the rotation axis.

In another aspect, the present invention provides a system for processing sample processing devices, the system including a base plate operatively coupled to a drive system, wherein the drive system rotates the base plate about a rotation axis; a cover facing a first surface of the base plate; compression structure operatively attached to the cover to force the cover towards the base plate; thermal structure operatively attached to the base plate; one or more resilient members operatively coupled to one or both of the cover and thermal structure, wherein the one or more resilient members provide a biasing force opposing the force of the compression structure forcing the cover towards the base plate, wherein a portion of a sample processing device located between the cover and the first surface of the base plate is urged into contact with the thermal structure; and an energy source adapted to deliver thermal energy to the thermal structure while the base plate is rotating about the rotation axis.

In another aspect, the present invention provides a method of processing sample material located within a sample processing device by locating a sample processing device between a base plate and a cover, wherein the sample processing device includes one or more process chambers located within an annular processing ring, and wherein a convex transfer surface is attached to the base plate, wherein the convex transfer surface is in the form of an annular ring that is in contact with the annular processing ring on the sample processing device; deforming the annular processing ring of the sample processing device on the convex transfer surface by forcing the cover and the base plate towards each other; and rotating the base plate, cover and sample processing device about an axis of rotation while deforming the annular processing ring on the convex transfer surface.

These and other features and advantages of the devices, systems and methods of the invention are described below with respect to illustrative embodiments of the invention.

DESCRIPTION OF EXEMPLARY
EMBODIMENTS OF THE INVENTION

In the following detailed description of exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention provides methods and systems for sample processing devices that can be used in methods that involve thermal processing, e.g., sensitive chemical processes such as PCR amplification, ligase chain reaction (LCR), self-sustaining sequence replication, enzyme kinetic studies, homogeneous ligand binding assays, and more complex biochemical or other processes that require precise thermal control and/or rapid thermal variations. The sample processing systems are capable of providing simultaneous rotation of the sample processing device in addition to control over the temperature of sample materials in process chambers on the devices.

Some examples of suitable sample processing devices that may be used in connection with the methods and systems of the present invention may be described in, e.g., commonly-assigned U.S. Pat. No. 6,734,401 titled ENHANCED SAMPLE PROCESSING DEVICES SYSTEMS AND METHODS (Bedingham et al.) and U.S. Pat. No. 7,026,168 titled SAMPLE PROCESSING DEVICES. Other useable device constructions may be found in, e.g., U.S. Provisional Patent Application Ser. No. 60/214,508 filed on Jun. 28, 2000 and entitled THERMAL PROCESSING DEVICES AND METHODS; U.S. Provisional Patent Application Ser. No. 60/214,642 filed on Jun. 28, 2000 and entitled SAMPLE PROCESSING DEVICES, SYSTEMS AND METHODS; U.S. Provisional Patent Application Ser. No. 60/237,072 filed on Oct. 2, 2000 and entitled SAMPLE PROCESSING DEVICES, SYSTEMS AND METHODS; U.S. Provisional Patent Application Ser. No. 60/260,063 filed on Jan. 6, 2001 and titled SAMPLE PROCESSING DEVICES, SYSTEMS AND METHODS; U.S. Provisional Patent Application Ser. No. 60/284,637 filed on Apr. 18, 2001 and titled ENHANCED SAMPLE PROCESSING DEVICES, SYSTEMS AND METHODS; and U.S. Pat. No. 6,814,935 titled SAMPLE PROCESSING DEVICES AND CARRIERS. Other potential device constructions may be found in, e.g., U.S. Pat. No. 6,627,159 titled CENTRIFUGAL FILLING OF SAMPLE PROCESSING DEVICES (Bedingham et al.)

The sample processing systems of the present invention preferably include base plates attached to a drive system in manner that provides for rotation of the base plate about an axis of rotation. When a sample processing device is secured to the base plate, the sample processing device is rotated with the base plate. The base plates include at least one thermal structure that can be used to heat portions of the sample processing devices and may include a variety of other components as well, e.g., temperature sensors, resistance heaters, thermoelectric modules, light sources, light detectors, transmitters, receivers, etc.

Although relative positional terms such as "top", "bottom", "above", "below", etc. may be used in connection with the present invention, it should be understood that those terms are used in their relative sense only. For example, when used in connection with the devices of the present invention, "top" and "bottom" may be used to signify opposing sides of the base plates, with the top surface typically located closest to the sample processing device mounted to the base plate during sample processing.

In actual use, elements described as "top" or "bottom" may be found in any orientation or location and should not be considered as limiting the methods, systems, and devices to any particular orientation or location. For example, the top surface of the sample processing device may actually be located below the bottom surface of the sample processing device during processing (although the top surface would still be found on the opposite side of the sample processing device from the bottom surface).

Figure 1:
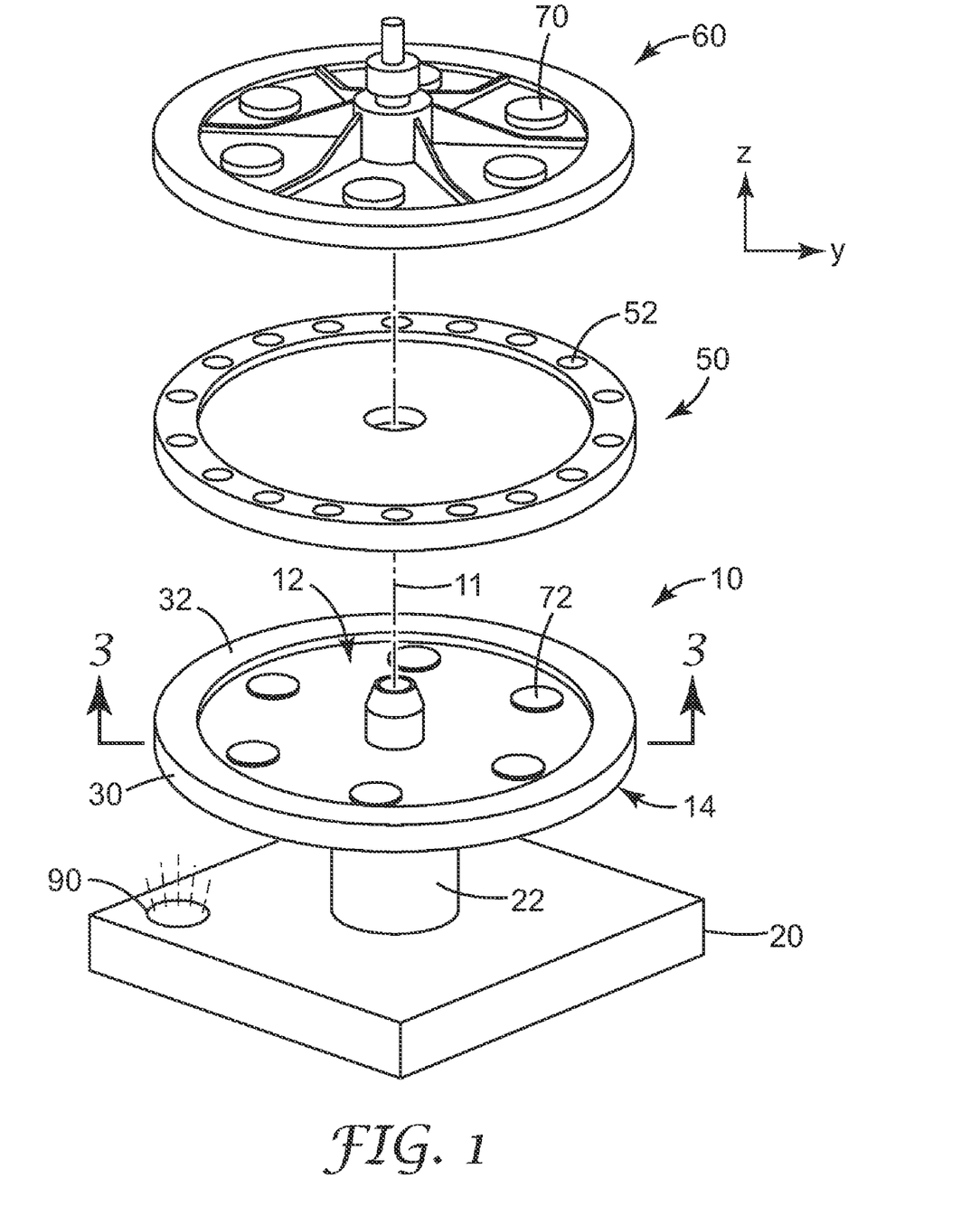
FIG. 1 is an exploded perspective view of one exemplary system according to the present invention depicting a base plate and cover with a sample processing device located therebetween.

One illustrative sample processing system is schematically depicted in the exploded perspective view of FIG. 1. The system includes a base plate 10 that rotates about an axis of rotation 11. The base plate 10 may preferably be attached to a drive system 20 through a shaft 22. It will, however, be understood that the base plate 10 may be coupled to the drive system 20 through any suitable alternative arrangement, e.g., belts or a drive wheel operating directly on the base plate 10, etc.

Also depicted in FIG. 1 is a sample processing device 50 and cover 60 that may preferably be used in connection with the base plate 10 as will be described herein. Systems of the present invention may not actually include a sample processing device as, in most instances, sample processing devices are consumable devices that are used to perform a variety of tests, etc. and then discarded. As a result, the systems of the present invention may be used with a variety of different sample processing devices.

The depicted base plate 10 includes a thermal structure 30 that preferably includes a transfer surface 32 exposed on the top surface 12 of the base plate 10. By "exposed" it is meant that the transfer surface 32 of the thermal structure 30 can be placed in physical contact with a portion of a sample processing device 50 such that the thermal structure 30 and the sample processing device are thermally coupled to transfer thermal energy through conduction. It may be preferred that the transfer surface 32 of the thermal structure 30 be located directly beneath selected portions of a sample processing device 50 during sample processing. The selected portions of the sample processing device 50 may preferably include process chambers 52 as discussed in, e.g., U.S. Pat. No. 6,734,401 titled ENHANCED SAMPLE PROCESSING DEVICES SYSTEMS AND METHODS (Bedingham et al.).

As discussed herein, the systems of the present invention may preferably include a cover 60 that, together with the base plate 10, compress a sample processing device located therebetween to preferably enhance thermal coupling between the thermal structure 30 on the base plate and the sample processing device 50. It may be preferred that both the sample processing device 50 and the cover 60 rotate with the base plate 10 as it is rotated about axis 11 by drive system 20.

The compressive forces developed between the base plate 10 and the cover 60 may be accomplished using a variety of different structures. One exemplary compression structure depicted in the embodiment of FIG. 1 are magnetic elements 70 located on the cover 60 and corresponding magnetic elements 72 located on the base plate 10. Magnetic attraction between the magnetic elements 70 and 72 may be used to draw the cover 60 and the base plate 10 towards each other, thereby compressing or deforming a sample processing device 50 located therebetween.

As used herein, a "magnetic element" is a structure or article that exhibits magnetic fields. The magnetic fields are preferably of sufficient strength to develop the desired compressive force that results in thermal coupling between a sample processing device 50 and the thermal structure 30 of base plate 10 as discussed herein. The magnetic elements may preferably include magnetic materials, i.e., materials that either exhibit a permanent magnetic field or that are capable of exhibiting a temporary magnetic field.

Some examples of potentially suitable magnetic materials include, e.g., magnetic ferrite or "ferrite" which is a substance including mixed oxides of iron and one or more other metals, e.g., nanocrystalline cobalt ferrite. However, other ferrite materials may be used. Other magnetic materials which may be utilized in the construction of the device 50 may include, but are not limited to, ceramic and flexible magnetic materials made from strontium ferrous oxide which may be combined with a polymeric substance (such as, e.g., plastic, rubber, etc.); NdFeB (this magnetic material may also include Dysprosium); neodymium boride; SmCo (samarium cobalt); and combinations of aluminum, nickel, cobalt, copper, iron, titanium, etc.; as well as other materials. Magnetic materials may also include, e.g., stainless steel or other magnetizable materials that may be rendered sufficiently magnetic by subjecting the magnetizable material to a sufficient electric and/or magnetic field.

It may be preferred that the magnetic elements 70 and 72 be discrete articles operably attached to the cover 60 and base plate 10 as depicted in the embodiment of FIG. 1 (in which the magnetic elements 70 and 72 are disc-shaped articles). In one alternative, however, the base plate 10, thermal structure 30, and/or cover 60 may contain sufficient magnetic material (e.g., molded or otherwise provided in the structure of the component) that separate, discrete magnetic elements are not required.

Figure 2:
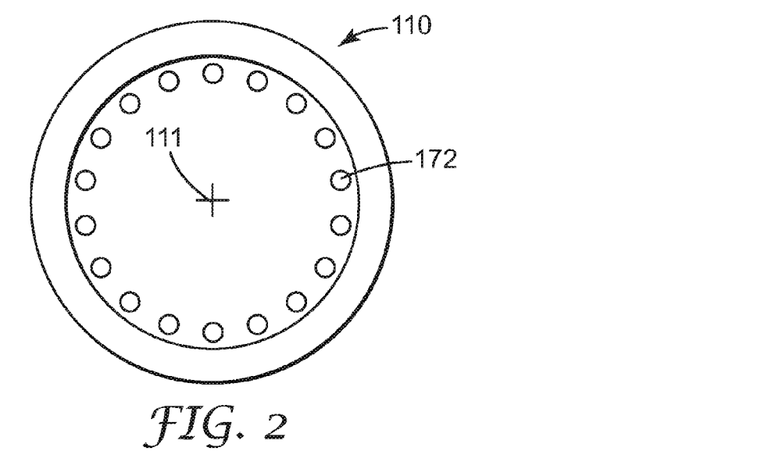
FIG. 2 is a plan view of an alternative arrangement of magnetic elements on a base plate according to the present invention.

FIG. 2 is a view of one alternative arrangement of magnetic elements 172 on an alternative base plate 110 that may preferably rotate about axis 111. As depicted in FIG. 2, the magnetic elements 172 may be smaller than those in the system depicted in FIG. 1. A potential advantage of such an arrangement may be found in a more uniform distribution of the magnetic force about the circumference of the base plate 110 (especially where the cover includes a complementary arrangement of magnetic elements).

In another alternative, the cover 60 and/or base plate 10 may include one or more magnetic elements in the form of electromagnets that can be activated as needed to provide the compressive force in place of passive magnetic elements. In such an embodiment, electric power would need to be provided to the electromagnets during rotation of the sample processing device 50.

Although not explicitly depicted in FIG. 1 the base plate 10 may preferably be constructed such that the thermal structure 30 is exposed on both the top and the bottom surfaces 12 and 14 of the base plate 10. By exposing the thermal structure 30 on the top surface 12 of the base plate 10, a more direct thermal path can be provided between the transfer surface 32 of the thermal structure 30 and a sample processing device 50 located between the cover 60 and the base plate 10.

The thermal structure 30 is also preferably exposed on the bottom surface 14 of the base plate 10. Exposing the thermal structure 30 on the bottom surface 14 of the base plate 10 may provide an advantage when the thermal structure 30 is to be heated by electromagnetic energy emitted by a source directing electromagnetic energy onto the bottom surface 14 of the base plate 10.

Although the system of FIG. 1 includes an electromagnetic energy source to deliver thermal energy to the thermal structure, the temperature of the thermal structure may be controlled by any suitable energy source that can deliver thermal energy to the thermal structure. Examples of potentially suitable energy sources for use in connection with the present invention other than electromagnetic energy sources may include, e.g., Peltier elements, electrical resistance heaters, etc.

As used in connection with the present invention, the term "electromagnetic energy" (and variations thereof) means electromagnetic energy (regardless of the wavelength/frequency) capable of being delivered from a source to a desired location or material in the absence of physical contact. Non-limiting examples of electromagnetic energy include laser energy, radio-frequency (RF), microwave radiation, light energy (including the ultraviolet through infrared spectrum), etc. It may be preferred that electromagnetic energy be limited to energy falling within the spectrum of ultraviolet to infrared radiation (including the visible spectrum).

One example of an electromagnetic energy source 90 is depicted in FIG. 1, with the electromagnetic energy emitted by the source 90 directed onto the bottom surface 14 of the base plate 10 and the portion of the thermal structure 30 exposed on the bottom surface 14 of the base plate 10. Examples of some suitable electromagnetic energy sources may include, but are not limited to, lasers, broadband electromagnetic energy sources (e.g., white light), etc.

Where the thermal structure 30 is to be heated by a remote energy source, i.e., an energy source that does not deliver thermal energy to the thermal structure by direct contact, the thermal structure 30 may preferably be constructed to absorb electromagnetic energy and convert the absorbed electromagnetic energy into thermal energy. The materials used in the thermal structure 30 preferably possess sufficient thermal conductivity and absorb electromagnetic energy generated by the electromagnetic source 90 at sufficient rates. In addition, it may also be desirable that the material or materials used for the thermal structures 30 have sufficient heat capacity to provide a heat capacitance effect. Examples of some suitable materials include, but are not limited to: aluminum, copper, gold, etc. If the thermal structure 30 is constructed of materials that do not, themselves, absorb electromagnetic energy at a sufficient rate, it may be preferred that the thermal structure 30 include a material that improves energy absorption. For example, the thermal structure 30 may be coated with an electromagnetic energy absorptive material such as carbon black, polypyrrole, inks, etc.

In addition to selection of suitable materials for the thermal structure 30, it may also be preferred to include grooves or other surface structure facing the electromagnetic energy source 90 to increase the amount of surface area exposed to the electromagnetic energy emitted by the source 90. Increasing the surface area of the thermal structure 30 exposed to the electromagnetic energy from source 90 may enhance the rate at which energy is absorbed by the thermal structure 30. The increased surface area used in the thermal structures 30 may also increase the efficiency of electromagnetic energy absorption.

It may further be desirable that the thermal structure 30 be relatively thermally isolated from the remainder of the base plate 10 such that only limited amounts (if any) of the thermal energy in the thermal structure 30 is transferred to the remainder of the base plate 10. That thermal isolation may be achieved, for example, by manufacturing the support structure of the base plate 10 of materials that absorb only limited amounts of thermal energy, e.g. polymers, etc. Some suitable materials for the support structure of base plate 10 include, e.g., glass-filled plastics (e.g., polyetheresterketone), silicones, ceramics, etc.

Although the base plate 10 includes a thermal structure 30 in the form of a substantially continuous circular ring, the thermal structures used in base plates of systems according to the present invention may alternatively be provided as a series of discontinuous thermal elements, e.g., circles, squares, located beneath process chambers on the sample processing device 50. One potential advantage, however, of a continuous ring thermal structure 30 is that temperature of the thermal structure 30 may equilibrate during heating. If a group of process chambers in a sample processing device are arranged such that they are in direct contact with the transfer surface 32 of the thermal structure 30, there is a potential to improve chamber-to-chamber temperature uniformity for all process chambers located above the continuous thermal structure 30.

Although the depicted base plate 10 includes only one thermal structure 30, it will be understood that base plates in the systems of the present invention could include any number of thermal structures that are necessary to transfer thermal energy to or from the selected process chambers in a sample processing device located thereon. Further, it may be preferred that, where more than one thermal structure is provided, the different thermal structures be independent of each other such that no significant amount of thermal energy is transferred between the different independent thermal structures. One example of an alternative in which independent thermal structures are provided may be in the form of concentric annular rings.

Figure 3:
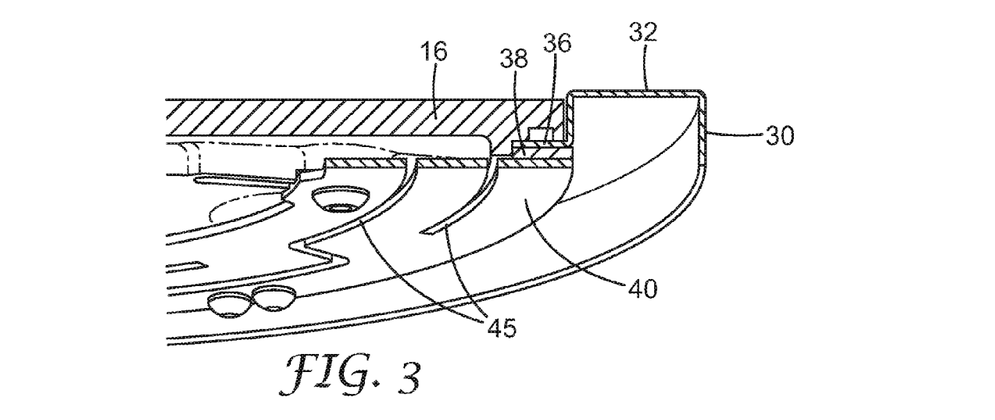
FIG. 3 is a perspective cross-sectional view of a portion of one base plate with a resiliently biased thermal structure according to the present invention.

FIG. 3 is a perspective cross-sectional view of a portion of the base plate 10 and thermal structure 30 of the system depicted in FIG. 1 taken along line 3-3 in FIG. 1. The base plate 10 includes main body 16 to which the thermal structure 30 is attached. Although not seen in FIG. 3, the main body 16 may preferably be fixedly attached to a spindle used to rotate the base plate 10. By fixedly attached, it is meant that the main body 16 preferably does not move relative to the spindle when a sample processing device is compressed between the cover 60 and the base plate 10 during operation of the system.

As depicted in FIG. 3, the thermal structure 30 may preferably be generally U-shaped below the transfer surface 32. Such shaping may preferably accomplish a number of functions. For example, the U-shaped thermal structure 30 may increase the surface area onto which electromagnetic energy is incident, thus potentially increasing the amount and rate at which energy is transferred to the thermal structure 30. In addition, the U-shaped thermal structure may present a lower thermal mass for the thermal structure 30.

As discussed herein, one optional feature of systems of the present invention is the floating or suspended attachment of the thermal structure 30 such that the thermal structure 30 and the cover 60 are resiliently biased towards each other. It may be preferred that the thermal structure 30 be coupled to the base plate 10 by one or more resilient members, with the one or more resilient members providing a biasing force opposing the force applied by the compression structure (e.g., magnets). In such a system, it may be preferred that the thermal structure 30 be capable of movement relative to the main body 16 of the base plate 10 in response to compressive forces between the base plate 10 and the cover 60. Movement of the thermal structure 30 may preferably be limited to a z-axis direction that is preferably aligned with (preferably parallel to) the axis of rotation. Such movement of the thermal structure may be described, e.g., in the following manner: the thermal structure is movable relative to the first surface of the base plate when a portion of a sample processing device located between the cover and the base plate is urged into contact with the transfer surface of the thermal structure.

Resilient coupling of the thermal structure 30 may be advantageous by providing improved compliance with the surface of the sample processing device 50. The floating attachment of the thermal structure 30 may help to compensate for, e.g., surfaces that are not flat, variations in thickness, etc. Resilient coupling of the thermal structure 30 may also improve uniformity in the compressive forces developed between the cover 60 and the thermal structure 30 when a sample processing device 50 is compressed between the two components.

Figure 4:
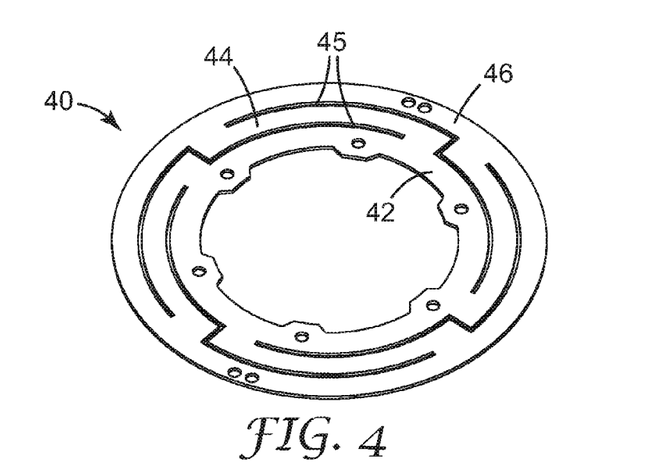
FIG. 4 is a perspective view of one exemplary biasing member that may be used in connection with the present invention.

Many different mechanisms may be used to resiliently couple the thermal structure 30. One exemplary mechanism is depicted in FIGS. 3 and 4 in the form of a flat spring 40 that is attached to the main body 16 and the thermal structure 30. The depicted flat spring 40 includes an inner ring 42 and spring arms 44 that extend to an outer ring 46. The inner ring 42 is attached to the main body 16 and the outer ring 46 is attached to a flange 36 on the thermal structure 30. Attachment of the spring 40 may be accomplished by any suitable technique or techniques, e.g., mechanical fasteners, adhesives, solder, brazing, welding, etc.

The forces generated by the flat spring 40 may be adjusted by changing the length of the cuts 45 defining the spring arms 44, changing the radial width of the spring arms 44, changing the thickness of the spring arms 44 (in the z-axis direction), selection of materials for the spring 40, etc.

It may be preferred that the force urging the base plate 10 and cover 60 towards each other result in physical contact between the main body 16 of the base plate 10 and the cover 60 within the circle bounded by the inner edge of the transfer surface 32 of the thermal structure 30. In other words, the magnetic attraction force in the depicted embodiment preferably draws the cover 60 against the main body 16 of the base plate 10. As a result, the forces exerted on the portion of the sample processing device 50 clamped between the cover 60 and the transfer surface 32 are exerted by the flat spring 40 (or other resilient members if used). In other words, control over the clamping force may preferably be controlled by the resilient member/flat spring 40.

To achieve the result described in the preceding paragraph it may be preferred that the clamping force generated between the cover 60 and the main body 16 of the base plate 10 be greater than the biasing force operating to force the transfer surface 32 of the thermal structure 30 towards the cover 60. As a result, the cover 60 is drawn into contact with the main body 16 and the resilient member (e.g., flat spring 40 in the depicted embodiment) controls the forces applied to the sample processing device 50 between the cover 60 and the transfer surface.

In the depicted embodiment an insulating element 38 is located between the outer ring 46 and the flange 36. The insulating element 38 may serve a number of functions. For example, the insulating element 38 may reduce the transfer of thermal energy between the outer ring 46 of the spring 40 and the flange 36 of the thermal structure 30. Another potential function of the insulating element 38 may be to provide a pre-load to the spring 40 such that the force with which the thermal structure 30 is biased towards the top surface 12 of the base plate 10 is at or above a selected level. A thicker insulating element 38 would typically be expected to increase the pre-load while a thinner insulating element 38 would typically be expected to reduce the pre-load. Examples of some potentially suitable materials for insulating element may include materials with lower thermal conductivity than metals, e.g., polymers, ceramics, elastomers, etc.

Although a flat spring 40 is one example of a resilient member that can be used to resiliently couple the thermal structure 30, many other resilient members could be used in place of or in addition to the depicted flat spring 40. Examples of some other potentially suitable resilient members may include, e.g., leaf springs, elastomeric elements, pneumatic structures (e.g., pistons, bladders, etc.), etc.

Although the flat spring 40 and the main body 16 of the base plate 10 are depicted as separate components in the exemplary embodiment of FIGS. 1 and 3, alternatives may be possible which the functions of the main body 16 and the spring 40 are accomplished in a single, unitary component.

Figure 5:
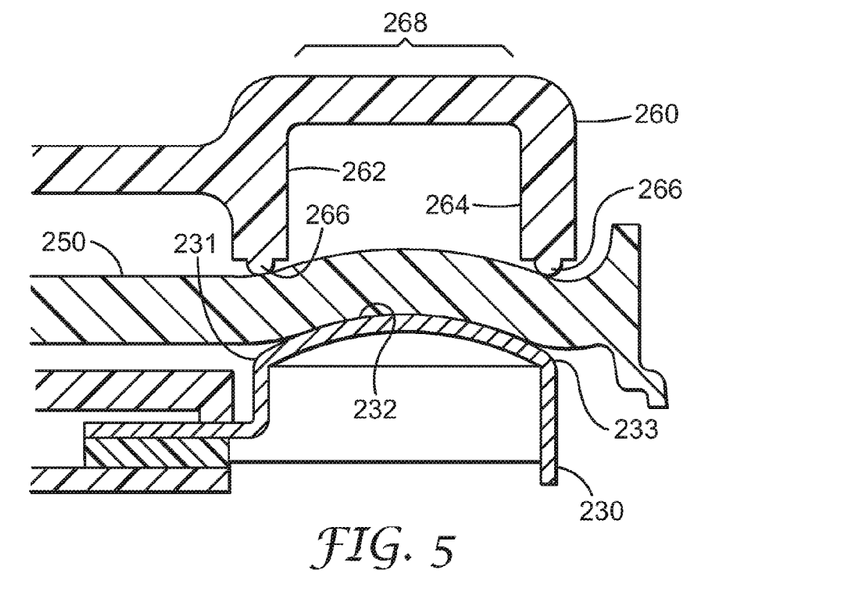
FIG. 5 is an enlarged cross-sectional view of a cover forcing a sample processing device to conform to a shaped transfer surface on a thermal structure according to the present invention.

One example of other optional features of sample processing systems of the present invention is depicted in connection with FIG. 5 which is an enlarged cross-sectional view of a sample processing device 250 held under compression between a thermal structure 230 and a cover 260.

In the embodiment seen in FIG. 5, the transfer surface 232 of the thermal structure 230 may preferably be a shaped surface with a raised portion located between an inner edge 231 and an outer edge 233 (where inner edge 231 is closest to the axis of rotation about which the thermal structure rotates as discussed herein). The raised portion of the transfer surface 232 may preferably be closer to the cover 260 than the portions of the thermal structure at the inner and outer edges 231 and 233 before the sample processing device 250 is contacted by the cover 260. The transfer surface 232 may preferably have a convex curvature when seen in a radial cross-section as depicted in FIG. 5. The convex transfer surface 232 may be defined by a circular curve or any other curved profile, e.g., elliptical, etc.

Figure 6:
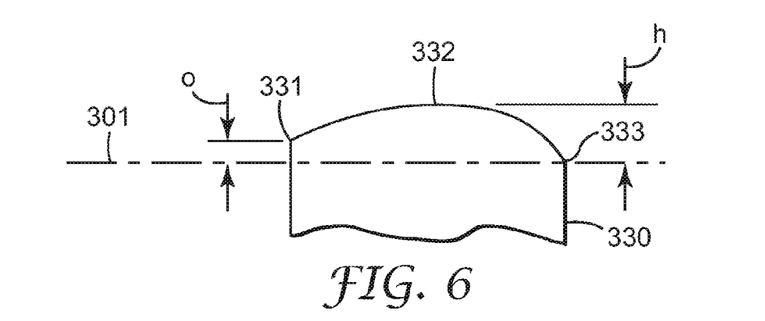
FIG. 6 is a diagram depicting the radial cross-sectional profile of one exemplary shaped thermal transfer surface that may be used in connection with the present invention.
Figure 7:
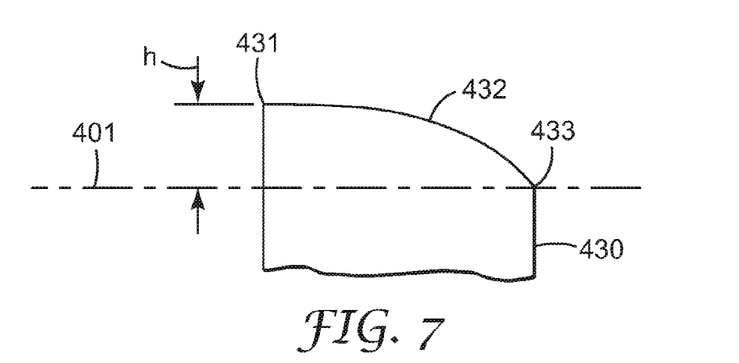
FIG. 7 is a diagram depicting the radial cross-sectional profile of another exemplary shaped thermal transfer surface that may be used in connection with the present invention.

FIGS. 6 and 7 depict alternative shaped transfer surfaces that may be used in connection with thermal structures that are provided as, e.g., annular rings. One such variation as depicted in FIG. 6 includes a thermal structure 330 (depicted in cross-section to illustrate its profile). The thermal structure 330 includes a shaped transfer surface 332 with an inner edge 331 and an outer edge 333. The inner edge 331 is located proximate an axis of rotation about which the thermal structure 330 is rotated as discussed herein. Also depicted is a plane 301 (seen on edge in FIG. 6) that is transverse to the axis of rotation.

In the depicted embodiment, the plane 301 extends through the outer edge 333 of the shaped transfer surface 332. Unlike the transfer surface 232 of FIG. 5 in which the inner and outer edges 231 and 233 are located on the same plane, the inner edge 331 of the transfer surface 332 may preferably be located at an offset (o) distance from the reference plane 301 as depicted in FIG. 6. It may be preferred that the inner edge 331 of the transfer surface 332 be located closer to the cover (not shown) than the outer edge 333.

As discussed herein, the shaped transfer surface 332 may preferably include a raised portion between the inner edge 331 and the outer edge 333. The height (h) of the raised portion is depicted in FIG. 6 relative to the plane 301, with the height (h) preferably representing the maximum height of the raised portion of the transfer surface 332.

Although the shaped transfer surfaces 232 and 332 depicted in FIGS. 5 and 6 include a raised portion with a maximum height located between the inner and outer edges of the transfer surfaces, the maximum height of the raised portion may alternatively be located at the inner edge of the transfer surface. One such embodiment is depicted in FIG. 7 in which a cross-sectional view of a portion of a thermal structure 430 is depicted. The thermal structure 430 includes a shaped transfer surface 432 with an inner edge 431 and an outer edge 433 as discussed above. The transfer surface 432 preferably includes a raised portion with a height (h) above a reference plane 401 that extends through the outer edge 433 of the transfer surface 432.

Unlike the transfer surfaces of FIGS. 5 and 6, however, the raised portion of the transfer surface 432 has its maximum height (h) located at the inner edge 431. From the maximum height (h), the transfer surface curves downward in a convex curve towards the outer edge 433. In such an embodiment, the inner edge 431 is located at an offset (o) distance from the reference plane 401 that is equal to the height (h).

The amount by which the transfer surfaces 232, 332, 432 deviate from a planar surface may be exaggerated in FIGS. 5-7. The height (h) may in some sense be a function of the radial distance from the inner edge to the outer edge of the transfer surface. For transfer surfaces with a radial width of, e.g., 4 centimeters or less, preferably 2 centimeters or less, and even 1 centimeter or less, it may be preferred that the height (h) be within a range with a lower value greater than zero, preferably 0.02 millimeters (mm) or more, more preferably 0.05 millimeters or more. At the upper end of the range, it may be preferred that the height (h) be 1 millimeter or less, preferably 0.5 mm or less, and even 0.25 millimeters or less.

Returning to FIG. 5, by providing a shaped transfer surface in connection with a cover 260 and compression structure of the present invention, thermal coupling efficiency between the thermal structure 230 and the sample processing device 250 may be improved. The shaped transfer surface 232 in combination with the force applied by the cover 260 may preferably deform the sample processing device 250 such that it conforms to the shape of the transfer surface 232. Such deformation of the sample processing device 250 may be useful in promoting contact even if the surface of the sample processing device 250 facing the transfer surface 232 or the transfer surface 232 itself include irregularities that could otherwise interfere with uniform contact in the absence of deformation.

If the sample processing device 250 includes process chambers (see, e.g., chambers 52 on sample processing device 50 in FIG. 1), it may be preferred to provide an optical window 268 in the cover 260 that allows transmission of electromagnetic energy through the cover 260. Such electromagnetic energy may be used to, e.g., monitor process chambers, interrogate process chambers, heat process chambers, excite materials in the process chambers, etc. By optical window, it is meant that the selected portion of the cover 260 transmits electromagnetic with selected wavelengths. That transmission may be through transmissive materials or through a void formed in the cover 260.

To further promote deformation of the sample processing device 250 to conform to the shape of the transfer surface 232, it may be preferred to include compression rings 262 and 264 in the cover 260, such that the rings 262 and 264 contact the sample processing device 250—essentially spanning the portion of the sample processing device 250 facing the transfer surface 232. It may be further preferred that substantially all compression force transfer between the cover 260 and the thermal structure 230 occurs through the inner and outer compression rings 262 and 264 of the cover 260.

Figure 8A:
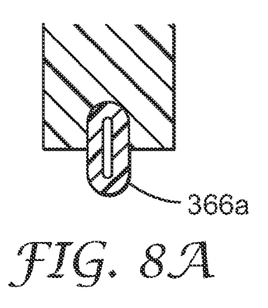
FIGS. 8A-8C depict alternative edge structures for compression rings on a cover according to the present invention.
Figure 8B:
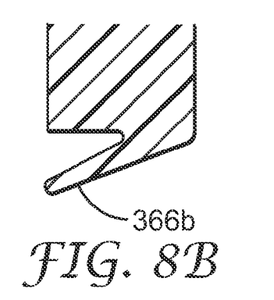
Figure 8C:
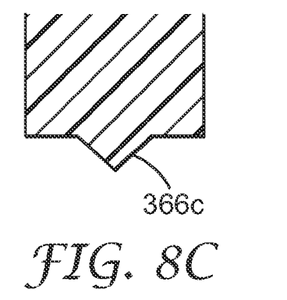

To potentially further enhance conformance of the sample processing device 250 to the transfer surface 232, it may be preferred that the inner and outer compression rings 262 and 264 include an edge treatment 266 such that minor variations in dimensions of the different components (cover, sample processing device, thermal structure, etc.) can be at least partially compensated for by the edge treatments 266. One example of suitable edge treatments may be a rounded structure that promotes point contact between the sample processing device 250 and the compression rings 262 and 264. Other potential examples of potentially suitable edge treatments may include, e.g., a resilient gasket 366a depicted in FIG. 8A, a cantilevered member 366b depicted in FIG. 8B, and a triangular structure 366c as depicted in FIG. 8C.

In another variation, it should be understood that although the depicted systems include resilient members coupling the thermal structures to the base plates, an alternative arrangement could be used in which the inner and outer compression rings 262 and 264 are resiliently coupled to the cover 260 by one or more resilient members. Resiliently mounting the compression rings 262 and 264 on the cover 260 may also serve to provide some compensation in the system for, e.g., surfaces that are not flat, variations in thickness, etc. Resilient coupling of the compression rings may also improve uniformity in the compressive forces developed between the cover 260 and the thermal structure 230 when a sample processing device 250 is compressed between the two components.

As discussed herein, it may be preferred that the portion of the sample processing device 250 in contact with the transfer surface 232 (or other shaped transfer surfaces) exhibit some compliance that, under compression, enables the sample processing device 250 to conform to the shape of the transfer surface 232. That compliance may be limited to the portions of the sample processing device located in contact with the transfer surface 232. Some potentially suitable sample processing devices that may include a compliant portion adapted to conform to a shaped thermal transfer surface are described in, e.g., U.S. Patent Application Publication No. US 2007/0009391, titled COMPLIANT MICROFLUIDIC SAMPLE PROCESSING DISKS, and U.S. Pat. No. 7,323,660, titled MODULAR SAMPLE PROCESSING APPARATUS AND METHODS.

Figure 9:
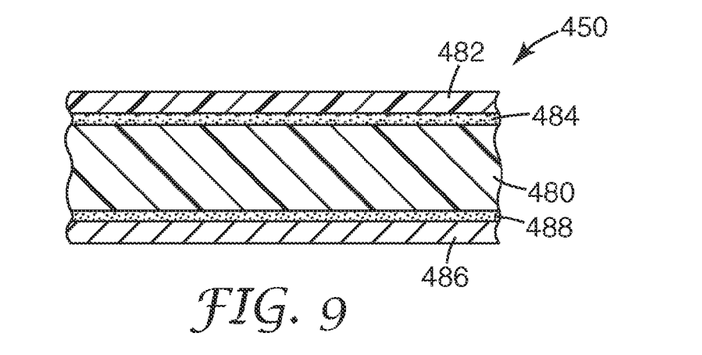
FIG. 9 is a cross-sectional view of a portion of a sample processing device that may be used in connection with the present invention.

As discussed in the documents identified in the preceding paragraph, compliance of sample processing devices may be enhanced if the devices include annular processing rings that are formed as composite structures including cores and covers attached thereto using pressure sensitive adhesives. A portion of one such composite structure is depicted in FIG. 9 which includes a device 450 having a body 480 to which covers 482 and 486 are attached using adhesives (preferably pressure sensitive adhesives) 484 and 488 (respectively). Where process chambers are provided in a circular array (as depicted in FIGS. 1 and 3) that is formed by a composite structure such as that seen in FIG. 9, the process chambers and covers may preferably define a compliant annular processing ring that is adapted to conform to the shape of an underlying thermal transfer surface when the sample processing disk is forced against a shaped thermal transfer surface. The compliance is preferably achieved with some deformation of the annular processing ring while maintaining the fluidic integrity of the process chambers (i.e., without causing leaks).

The body 480 and the different covers 482 and 486 used to seal any fluid structures (such as process chambers) in the sample processing devices may be manufactured of any suitable material or materials. Examples of suitable materials may include, e.g., polymeric materials (e.g., polypropylene, polyester, polycarbonate, polyethylene, etc.), metals (e.g., metal foils), etc. The covers may preferably, but not necessarily, be provided in generally flat sheet-like pieces of, e.g., metal foil, polymeric material, multi-layer composite, etc. It may be preferred that the materials selected for the body and the covers of the disks exhibit good water barrier properties.

It may be preferred that at least one of the covers 482 and 486 be constructed of a material or materials that substantially transmit electromagnetic energy of selected wavelengths. For example, it may be preferred that one of the covers 482 and 486 be constructed of a material that allows for visual or machine monitoring of fluorescence or color changes within the process chambers.

It may also be preferred that at least one of the covers 482 and 486 include a metallic layer, e.g., a metallic foil. If provided as a metallic foil, the cover may preferably include a passivation layer on the surface that faces the interior of the fluid structures to prevent contact between the sample materials and the metal. Such a passivation layer may also function as a bonding structure where it can be used in, e.g., hot melt bonding of polymers. As an alternative to a separate passivation layer, any adhesive layer used to attach the cover to the body 480 may also serve as a passivation layer to prevent contact between the sample materials and any metals in the cover.

In some embodiments, one cover 482 may preferably be manufactured of a polymeric film (e.g., polypropylene) while the cover 486 on the opposite side of the device 450 may preferably include a metallic layer (e.g., a metallic foil layer of aluminum, etc.). In such an embodiment, the cover 482 preferably transmits electromagnetic radiation of selected wavelengths, e.g., the visible spectrum, the ultraviolet spectrum, etc. into and/or out of the process chambers while the metallic layer of cover 486 facilitates thermal energy transfer into and/or out of the process chambers using thermal structures/surfaces as described herein.

The covers 482 and 486 may be attached to the body 480 by any suitable technique or techniques, e.g., melt bonding, adhesives, combinations of melt bonding and adhesives, etc. If melt bonded, it may be preferred that both the cover and the surface to which it is attached include, e.g., polypropylene or some other melt bondable material, to facilitate melt bonding. It may, however, be preferred that the covers 482 and 486 be attached using pressure sensitive adhesive. The pressure sensitive adhesive may be provided in the form of a layer of pressure sensitive adhesive that may preferably be provided as a continuous, unbroken layer between the cover and the opposing surface of the body 480. Examples of some potentially suitable attachment techniques, adhesives, etc. may be described in, e.g., U.S. Pat. No. 6,734,401 titled ENHANCED SAMPLE PROCESSING DEVICES SYSTEMS AND METHODS (Bedingham et al.) and U.S. Pat. No. 7,026,168 titled SAMPLE PROCESSING DEVICES.

Pressure sensitive adhesives typically exhibit viscoelastic properties that may preferably allow for some movement of the covers relative to the underlying body to which the covers are attached. The movement may be the result of deformation of the annular processing ring to, e.g., conform to a shaped transfer surface as described herein. The relative movement may also be the result of different thermal expansion rates between the covers and the body. Regardless of the cause of the relative movement between covers and bodies in the disks of the present invention, it may be preferred that the viscoelastic properties of the pressure sensitive adhesive allow the process chambers and other fluid features of the fluid structures to preferably retain their fluidic integrity (i.e., they do not leak) in spite of the deformation.

Sample processing devices that include annular processing rings formed as composite structures using covers attached to bodies with viscoelastic pressure sensitive adhesives may, as described herein, exhibit compliance in response to forces applied to conform the annular processing rings to shaped transfer surfaces. Compliance of annular processing rings in sample processing devices used in connection with the present invention may alternatively be provided by, e.g., locating the process chambers in an (e.g., circular) array within the annular processing ring in which a majority of the area is occupied by voids in the body 480. The process chambers themselves may preferably be formed by voids in the body 480 that are closed by the covers 482 and 486 attached to the body 480.

Figure 10:
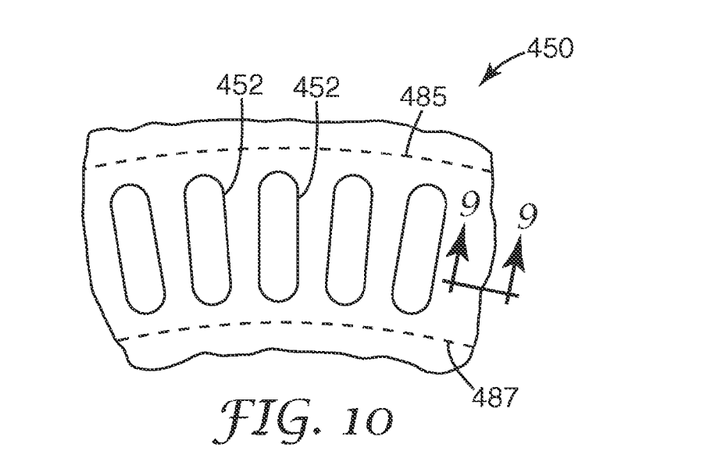
FIG. 10 is an enlarged plan view of a portion of the sample processing device of FIG. 9.

FIG. 10 is a plan view of a portion of one major surface of a sample processing device of the present invention. The portion of the device 450 depicted in FIG. 10 includes a portion of an annular processing ring having an outer edge 485 and an inner edge 487. Process chambers 452 are located within the annular processing ring and, as discussed herein, may preferably be formed as voids that extend through the body 480, with the covers 482 and 486 defining the volume of the of the process chambers 452 in connection with the voids. To improve compliance or flexibility of the annular processing ring occupied by the process chambers 452, it may be preferred that the voids of the process chambers 452 occupy 50% or more of the volume of the body 480 located within the annular processing ring.

It may be preferred that the inner compression ring (see reference no. 262 in FIG. 6) contact the device 450 along the inner edge 487 of the annular processing ring or between the inner edge 487 and the innermost portion of the process chambers 452. It may also be preferred that the outer compression ring (see reference no. 264 in FIG. 6) contact the device 450 along the outer edge 485 of the annular processing ring or between the outer edge 485 and the outermost portion of the process chambers 452.

Compliance of the annular processing rings in sample processing devices used in connection with the present invention may preferably be provided by a combination of an annular processing ring formed as a composite structure using viscoelastic pressure sensitive adhesive and voids located within the annular processing ring. Such a combination may provide more compliance than either approach taken alone.

As used herein and in the appended claims, the singular forms "a," "and," and "the" include plural referents unless the context clearly dictates otherwise. Thus, for example, reference to "a" or "the" component may include one or more of the components and equivalents thereof known to those skilled in the art.

All references and publications cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

The invention claimed is:

1. A system for processing sample processing devices, the system comprising:
    a base plate operatively coupled to a drive system, wherein the drive system rotates the base plate about a rotation axis, wherein the rotation axis defines a z-axis;
    thermal structure operatively attached to the base plate, wherein the thermal structure comprises a transfer surface exposed proximate a first surface of the base plate;
    a cover facing the transfer surface, wherein the cover comprises an inner compression ring and an outer compression ring;

a sample processing device adapted to be located between the cover and the base plate, a portion of the sample processing device comprising a plurality of process chambers;

compression structure operatively attached to the cover to force the cover in a first direction along the z-axis towards the transfer surface, wherein the inner and outer compression rings contact and urge the portion of the sample processing device into contact with the transfer surface;

one or more resilient members operatively coupled to one or both of the cover and thermal structure, wherein the one or more resilient members provide a biasing force opposing the force of the compression structure forcing the cover towards the base plate; and an energy source adapted to deliver thermal energy to the thermal structure while the base plate is rotating about the rotation axis.

2. A system according to claim 1, wherein the exposed transfer surface comprises a convex transfer surface in the form of an annular ring.

3. A system according to claim 1, wherein the exposed transfer surface is in the form of an annular ring that comprises an inner edge and an outer edge proximate the first surface of the base plate, wherein the outer edge of the transfer surface is offset in the first direction along the z-axis relative to the inner edge of the transfer surface.

4. A system according to claim 1, wherein substantially all compression force transfer between the cover and the thermal structure occurs through the inner compression ring and the outer compression ring.

5. A system according to claim 1, wherein the one or more resilient members couple the thermal structure to the base plate.

6. A system according to claim 5, wherein the thermal structure is movable relative to the first surface of the base plate when a portion of a sample processing device located between the cover and the base plate is urged into contact with the transfer surface of the thermal structure.

7. A system according to claim 5, wherein the one or more resilient members comprise a flat spring.

8. A system according to claim 3, wherein the exposed transfer surface comprises a raised portion having a maximum height located between the inner edge and the outer edge of the annular ring.

9. A system according to claim 1, wherein the compression structure comprises one or more magnetic elements operatively attached to the cover and base plate, wherein magnetic attraction between the one or more magnetic elements attached to the cover and the base plate draw the cover towards the first surface of the base plate.

10. A system according to claim 9, wherein the one or more magnetic elements comprise permanent magnets.

11. A system according to claim 9, wherein the one or more magnetic elements comprise a first set of permanent magnets operatively attached to the cover and a second set of permanent magnets operatively attached to the base plate.

12. A system according to claim 9, wherein the one or more magnetic are arranged in an annular ring and positioned radially inwardly of the plurality of process chambers.

13. A system according to claim 1, wherein the cover includes a portion located between the inner compression ring and the outer compression ring, and wherein the portion includes an optical window.

14. A system according to claim 1, wherein the energy source comprises an electromagnetic energy source adapted to direct electromagnetic energy onto a portion of the thermal structure while the base plate is rotating about the rotation axis.

15. A system for processing sample processing devices, the system comprising:

a base plate operatively coupled to a drive system, wherein the drive system rotates the base plate about a rotation axis, wherein the rotation axis defines a z-axis;

thermal structure operatively attached to the base plate, wherein the thermal structure comprises a transfer surface exposed proximate a first surface of the base plate;

a cover facing the transfer surface;

a sample processing device adapted to be located between the cover and the base plate, a portion of the sample processing device comprising a plurality of process chambers;

one or more magnetic elements operatively attached to the cover and base plate, wherein magnetic attraction between the one or more magnetic elements attached to the cover and the base plate draw the cover in a first direction along the z-axis towards the first surface of the base plate such that the portion of the sample processing device is urged into contact with the thermal structure of the base plate;

one or more resilient members operatively coupled to one or both of the cover and thermal structure, wherein the one or more resilient members provide a biasing force opposing the magnetic attraction drawing the cover towards the first surface of the base plate; and an energy source adapted to deliver thermal energy to the thermal structure while the base plate is rotating about the rotation axis.

16. A system according to claim 15, wherein the one or more magnetic elements comprise permanent magnets.

17. A system according to claim 15, wherein the one or more magnetic elements comprise a first set of permanent magnets operatively attached to the cover and a second set of permanent magnets operatively attached to the base plate.

18. A system according to claim 15, wherein the one or more magnetic are arranged in an annular ring and positioned radially inwardly of the plurality of process chambers.

19. A system according to claim 15, wherein the cover includes an optical window positioned adjacent the portion of the sample processing device when the sample processing device is located between the cover and the base plate.

20. A system according to claim 15, wherein the exposed transfer surface is in the form of an annular ring that comprises an inner edge and an outer edge proximate the first surface of the base plate, and wherein the exposed transfer surface comprises a raised portion having a maximum height located between the inner edge and the outer edge of the annular ring.

21. A system for processing sample processing devices, the system comprising:

a base plate operatively coupled to a drive system, wherein the drive system rotates the base plate about a rotation axis;

a cover facing a first surface of the base plate;

compression structure operatively attached to the cover to force the cover towards the base plate;

thermal structure operatively attached to the base plate;

a sample processing device adapted to be located between the cover and the base plate, a portion of the sample processing device comprising a plurality of process chambers;

one or more resilient members operatively coupling the thermal structure to the base plate, wherein the one or more resilient members provide a biasing force opposing the force of the compression structure forcing the cover towards the base plate, wherein the portion of the sample processing device is urged into contact with the thermal structure; and an energy source adapted to deliver thermal energy to the thermal structure while the base plate is rotating about the rotation axis.

22. A system according to claim 21, wherein the one or more resilient members comprise a flat spring.

23. A system according to claim 21, wherein the cover includes an optical window positioned adjacent the portion of the sample processing device when the sample processing device is located between the cover and the base plate.

24. A system for processing sample processing devices, the system comprising:

a base plate operatively coupled to a drive system, wherein the drive system rotates the base plate about a rotation axis, wherein the rotation axis defines a z-axis;

thermal structure operatively attached to the base plate, wherein the thermal structure comprises a transfer surface exposed proximate a first surface of the base plate, wherein the exposed transfer surface is in the form of an annular ring that comprises an inner edge and an outer edge proximate the first surface of the base plate, wherein the outer edge of the transfer surface is offset in the first direction along the z-axis relative to the inner edge of the transfer surface;

a cover facing the transfer surface, wherein the cover comprises an inner compression ring and an outer compression ring;

a sample processing device adapted to be located between the cover and the base plate, a portion of the sample processing device comprising a plurality of process chambers;

compression structure operatively attached to the cover to force the cover in a first direction along the z-axis towards the transfer surface, wherein the inner and outer compression rings contact and urge the portion of the sample processing device into contact with the transfer surface; and an energy source adapted to deliver thermal energy to the thermal structure while the base plate is rotating about the rotation axis.

* * * * *